United States Patent [19]

Oseroff et al.

[11] Patent Number: 4,651,739
[45] Date of Patent: Mar. 24, 1987

[54] LIGHT-INDUCED KILLING OF CARCINOMA CELLS

[75] Inventors: Allan Oseroff, Brookline; James Foley; Louis Cincotta, both of Andover; John A. Parrish, Weston, all of Mass.

[73] Assignee: The General Hospital Corporation, Boston, Mass.

[21] Appl. No.: 720,711

[22] Filed: Apr. 8, 1985

[51] Int. Cl.⁴ ............................................. A61N 5/00
[52] U.S. Cl. .................................................... 128/395
[58] Field of Search .................... 128/303.1, 362, 395, 128/633, 634, 653, 654

[56] References Cited

U.S. PATENT DOCUMENTS

| | | | |
|---|---|---|---|
| 4,181,128 | 1/1980 | Swartz | 128/362 |
| 4,336,809 | 6/1982 | Clark | 128/303.1 |
| 4,512,762 | 4/1985 | Spears | 128/303.1 |

OTHER PUBLICATIONS

"Analysis of ... and Reversability", by M. Nass, Cancer Res, vol. 44, pp. 2677–2684 Jun. 1984.
"Determination of Carbocyanine ... Disease States" by E. Sato et al., vol. 36, pp. 2750–2753, Aug. 1976.
"Porphyrins" by A. Vanarotti; Hilgen & Watts, Ltd., London, 1954, pp. 18, 19, 24, 25, 72 & 73.
"Photoradiation Therapy for the Treatment of Malignant Tumors", by T. Doughtery et al., Cancer Res, vol. 38, pp. 2628–2635, Aug. 1978.
"Rhodamine-123 Selectively Reduces Clonal Growth of Carcinoma Cells in Vitro", by S. Bernal et al; Science, vol. 218, pp. 1117–1119.
McKenzie (1985) Phys. in Med. Biol. 30:99.
Svaasand (1984) J. Op. Soc. Am. 1:555.
Tatsuta (1984) JNCL 731:59.
Dougherty et al., (1983) Adv. Exp. Med. Bio. 160:3.
Ambesi-Impiombato et al., in *Porphyrins in Tumor Phototherapy*, ed. Andreoni et al., Plenum Press, N.Y. (1984), pp. 143–156 Bernal et al. (1982) Science 220:117.
Anderson et al. (1983) Science 220:524.
Uzdensky (1982) Tsitologiia 24:119.
Gregorie et al. (1968) Annals of Surg. 167:820.
Cubeddu et al. (1984) J. Op. Soc. Am. B. 1:556.
Tanaka (1969) J. Cell. Biol. 41:424.
Parrish (1981) J. Investigative Dermatology 77:45.

*Primary Examiner*—Lee S. Cohen
*Assistant Examiner*—David Shay

[57] ABSTRACT

A method of killing carcinoma cells associated normal cells using light of a predetermined wavelength. The method includes contacting the cells with a chromophor at a given concentration. The chromophor is positively charged and sufficiently lipophilic to be taken up by the mitochondria of the carcinoma cells and is retained substantially longer in the mitochondria of carcinoma cells than in normal cell mitochondria; or it may be taken up in greater quantity by the carcinoma cells than by the normal cells. The chromophor must also have a therapeutic index for light-induced cell killing of at least 500 for light of the predetermined wavelength, and has a therapeutic ratio for light-induced killing of at least 50 for light of said pre-determined wavelength. The cells are then exposed to light of this wavelength.

5 Claims, 3 Drawing Figures

LIGHT-INDUCED KILLING OF CARCINOMA CELLS

BACKGROUND OF THE INVENTION

This invention relates to light-induced killing of carcinoma cells.

The literature contains a number of reports of cancer therapy employing lasers in conjunction with compounds, e.g., hematoporphyrins, which sensitize the cancer cells to laser light; examples are McKenzie (1985) Phys. in Med. Biol. 30, 99; Cubedda et al. (1984) J. Op. Soc. Am. 1, 556; Svaasand (1984) J. Op. Soc Am. 1, 555; and Tatsuta et al. (1984) JNCL 731, 59; the latter says that a hematoporphyrin derivative (HPD) "tends to accumulate in neoplastic tissue," citing three references. There have also been reports of non-specific phototoxicity caused by the accumulation of HPD in skin and other tissues (Dougherty et al. (1983) Adv. Exp. Med. Bio. 160, 3; Ambesi-Impiombato et al. in *Porphyrins in Tumor Phototherapy*, ed. Andreoni et al., Plenum Press, N.Y. (1984) pp. 143-156), and HPD has generally exhibited little selectivity for cancer cells compared to normal cells in vitro.

SUMMARY OF THE INVENTION

The invention features, in general, a method of killing carcinoma cells associated with normal cells using light (most preferably laser light) of predetermined wavelength; the method involves (a) contacting the cells with a chromophore, at a predetermined concentration, which is positively charged and sufficiently lipophilic to be taken up by the carcinoma cells and their mitochondria, which is taken up greater amounts and/or retained substantially longer in the mitochondria of the carcinoma cells than in the mitochondria of the normal cells, and which has a therapeutic index (as defined below) for light-induced cell killing of at least 500 for the light; and (b) exposing the carcinoma cells to the light.

Preferably, the chromophore also has a therapeutic ratio (as defined below) for light-induced cell killing of at least 50 for the light.

Where the chromophore is taken up by normal cells as well as by carcinoma cells, there is a time interval between steps (a) and (b) which is sufficiently long to permit dissipation from the normal cells of a sufficient amount of the chromophore to prevent killing of at least 80% of the normal cells contacted with the chromophore when the cells are exposed to the light, and sufficiently short to ensure that enough of the chromophore is retained by the mitochondria of the carcinoma cells to cause at least 80% of the carcinoma cells contacted with the chromophore to be killed when exposed to the light.

The invention provides rapid killing of carcinoma cells while doing minimal damage to surrounding healthy tissue, owing primarily to preferential uptake and/or retention of the chromophores by carcinoma mitochondria, compared to normal cells, and to the high therapeutic index of the chromophore.

Other features and advantages of the invention will be apparent from the following description of the preferred embodiments thereof, and from the claims.

DESCRIPTION OF THE PREFERRED EMBODIMENTS

The drawings will first be described.

Drawings

The chromophores and their therapeutic applications will now be described in more detail.

Uptake and Retention by Carcinoma Cells

To be concentrated across the carcinoma cell surface and carcinoma mitochondrial membrane, the chromophores must have one or more delocalized positive charges in aqueous solution, and must be fairly lipophilic. High retention and uptake (as well as low antigenicity) are also facilitated by a low molecular weight, i.e., below 1,000. The chemical structures and names of eight suitable chromophores possessing these characteristics are given in Table I, below; compound 8, the currently most preferred chromophore, has the chemical name 1,1'-(2-ethyl)-1,3 dioxolane kryptocyanine ("EDKC"). The chromophores listed in Table I were selected from a number of chromophores which were synthesized and screened for suitable therapeutic index and ratio; the compounds which failed to demonstrate suitably high such index and ratio, and which are thus not be useful in the practice of the invention, have been omitted from Table I; hence the gaps in the numbering of the chromophores.

TABLE I

Photochemical Characteristics of Some Potential Selective Chromophores

| Dye[a,b] | $\lambda_{max}$ | $\epsilon \times 10^{-4}$ (M$^{-1}$ cm$^{-1}$) | $\phi_d \times 10^{-3e}$ | $\phi(^1O_2)^f$ |
|---|---|---|---|---|
| (1) 1,1',3,3,3',3'-Hexamethylindodicarbocyanine Iodide | 632[c] 635[d] | 11.4 34.2 | 0.775 0.010 | 0.0 0.0 |
| 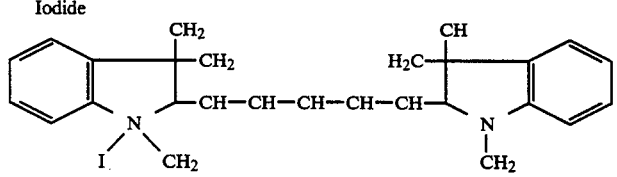 | | | | |
| (4) 3,3-Diethyloxatricarbocyanine Iodide | 675[c] | 9.0 | 1.207 | 0.0 |
| 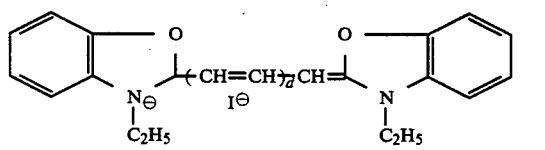 | | | | |

TABLE I-continued

Photochemical Characteristics of Some Potential Selective Chromophores

| Dye[a,b] | λmax | ε × 10$^{-4}$ (M$^{-1}$ cm$^{-1}$) | $\phi_d$ × 10$^{-3e}$ | $\phi(^1O_2)$[f] |
|---|---|---|---|---|
| (5) 1,1'-(3-Propylamine hydrobromide)-3,3,3',3'-tetramethylindole-tricarbocyanine | 735[c] 745[d] | 10.0 12.0 | 0.282 0.0 | 0.0 0.0 |
| (6) 1,1'-(3-Propylamine,3'-butylsulfonic acid) carbocyanine | 700[c] 708[d] | 1.3 5.3 | 4.08 0.223 | 0.0 0.0 |
| (7) 1,1'-ethylvalerate thiacarbocyanine bromide | 555[c] | 4.9 | 2.36 | 0.0 |
| (8) 1,1'-(2-ethyl)-1,3-dioxolane-kryptocyanine bromide (EDKC) | 630[g],700[c] 710[d] | 4.2 27.2 | 1.79 0.021 | 0.0 0.0 |
| (10) Tetrabrominated Rhodamine 123 | 510[c] | 8.0 | 0.837 | 0.91 |
| (12) Rhodamine 6 G | 530[c] | 8.4 | 0.279 | 0.0 |

TABLE I-continued
Photochemical Characteristics of Some Potential Selective Chromophores

| Dye[a,b] | λmax | $\epsilon \times 10^{-4}$ ($M^{-1} cm^{-1}$) | $\phi_d \times 10^{-3e}$ | $\phi(^1O_2)$[f] |
|---|---|---|---|---|
| [structure: H5C2NH-, H2C-, O, ⊕NHC2H5, CH3, Cl⊖, CO2C2H5, 12'] | 530[d] | 11.4 | 0.0 | 0.0 |

Figure 1:
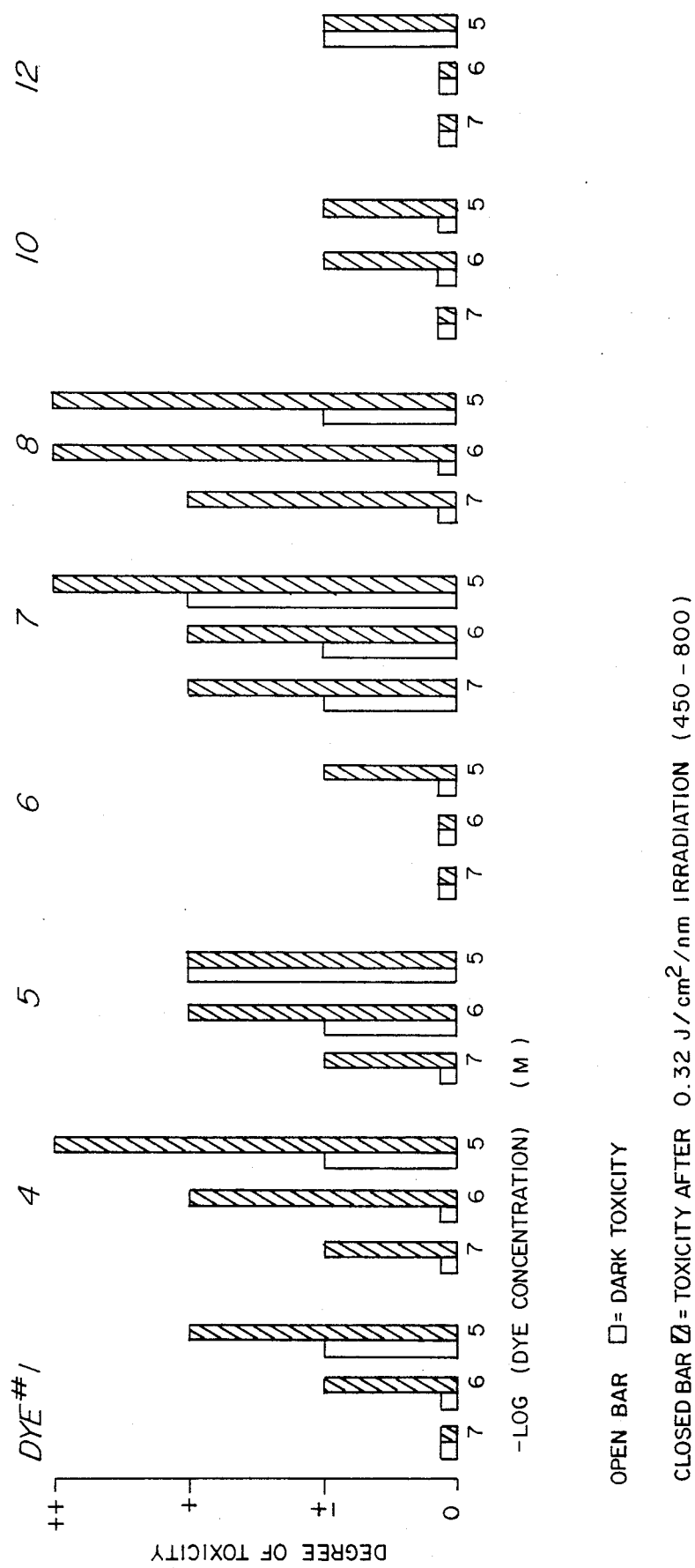
FIG. 1 is a graph showing dark and light toxicity of chromophores at three concentrations.

KEY:
[a]Chemical structure shown in FIG. 1.
[b]Molecular weights of dyes range between 500-100
[c]Phospate Buffered Saline.
[d]Methyl Alcohol.
[e]Quantum yield for photodecomposition, ($\phi_d = 0.0$ implies $< 10^{-4}$).
[f]Quantum yield for singlet oxygen generation.
[g]Aggregate peak absorbance of monomer and aggregate bands were comparable.

For reasons which are not fully understood, most chromophores which satisfy the above criteria can, unlike HPD, be expected to be preferentially taken up and retained in the mitochondria of carcinoma cells for substantially longer (three times as long or longer) periods of time than in normal cells. Generally, most such chromophores will have dissipated from normal cells after four to eight hours to a degree rendering those cells comparatively invulnerable to destruction by light, while carcinoma cells retain sufficient dye for light-induced killing for 24 hours or longer. ("Dye" and "chromophore" are used interchangeably herein.)

Protection of Normal Cells

The chromophores used in the method of the invention preferably have a therapeutic index for killing carcinoma cells (toxicity of dye+light:toxicity of dye—-light) of at least 500. They also preferably have a therapeutic ratio of killing carcinoma cells to normal cells (toxicity of dye+light in carcinoma cells:toxicity of dye+light in normal cells) of at least 50, using equal dye and light exposures for both cell types. The high therapeutic ratio and index, due, respectively, to selective mitochondrial retention and light-induced killing, prevent normal cells in the vicinity of the carcinoma cells from being substantially damaged, and permits the use of low, safe chromophore concentrations. Generally, the method employs a chromophore concentration which is at least 10 times lower than the "++" toxic (defined below) dose for normal cells in the absence of light. Photochemical killing of carcinoma cells with EDKC, for example, can be carried out using an EDKC concentration $10^2$-$10^3$ times lower than the concentration which is "++" toxic to normal cells in the absence of light.

The high therapeutic index of EDKC and of the other chromophore of Table I in part responsible for the ability to employ low therapeutic dosages, was demonstrated in an experiment, the results of which are shown in FIG. 1 (chromophore numbers correspond to the numbers of Table I). Sub-confluent cultures of EJ (MGH-U1) bladder carcinoma cells were incubated with each of the chromophores for 20 minutes at 37° C., washed and, after four hours, irradiated at room temperature with a broad band 1,000 watt xenon arc lamp source which was filtered to produce an output of about $0.5 \times 10^{-3}$ watts/cm$^2$/nm (500-800 nm). After irradiation, the cells were washed again and returned to the incubator for 48 hours. Toxicity (manifested as cell count, morphology, and viability) was evaluated microscopically; degree of toxicity was evaluated as "0" (identical to untreated control); "±" (less than 20% cell death and minimal morphological changes such as rounding up and vacuolization); "+" (20-60% cell death and moderate morphological changes); and "++" (greater than 60% cell death and marked morphological changes). As shown in FIG. 1, the chromophores exhibit high toxicity indexes at low concentrations.

Figure 2:
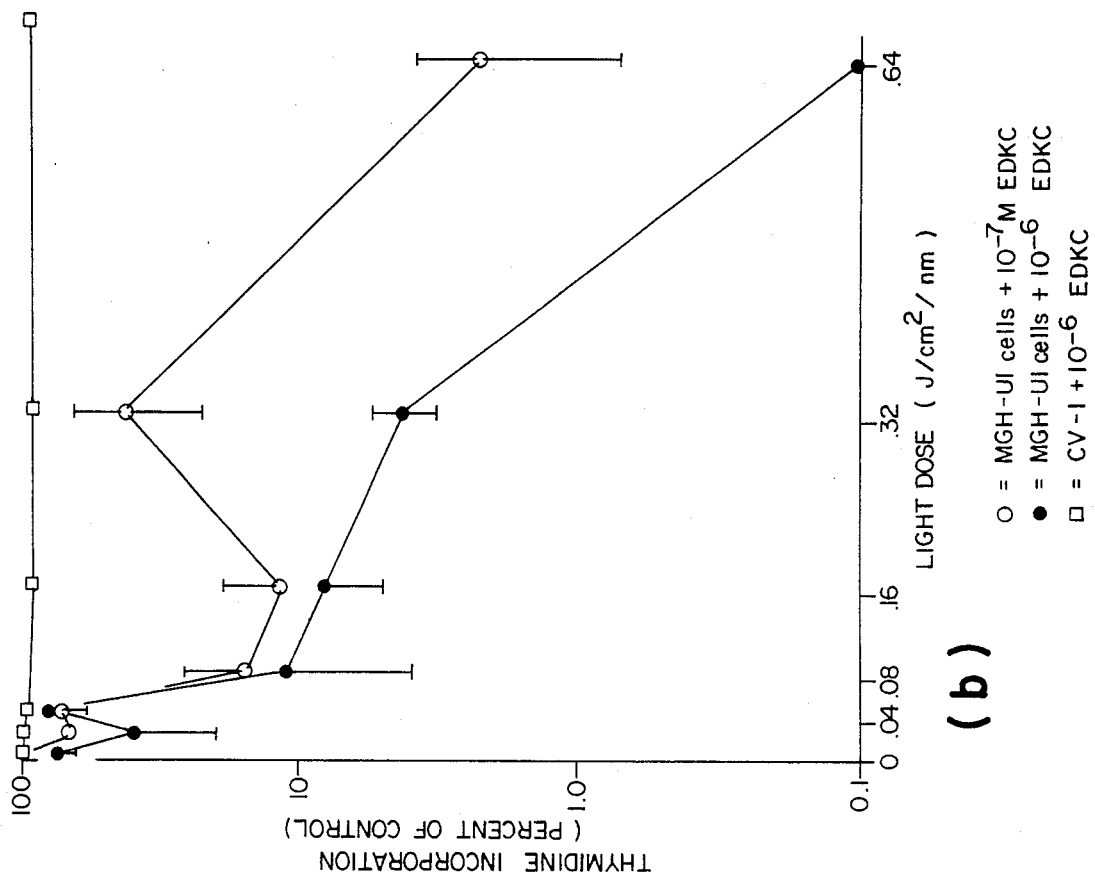
FIG. 2 is a pair of graphs illustrating preferential light-induced toxicity to carcinoma cells of one chromophore of the invention.
Figure 2:
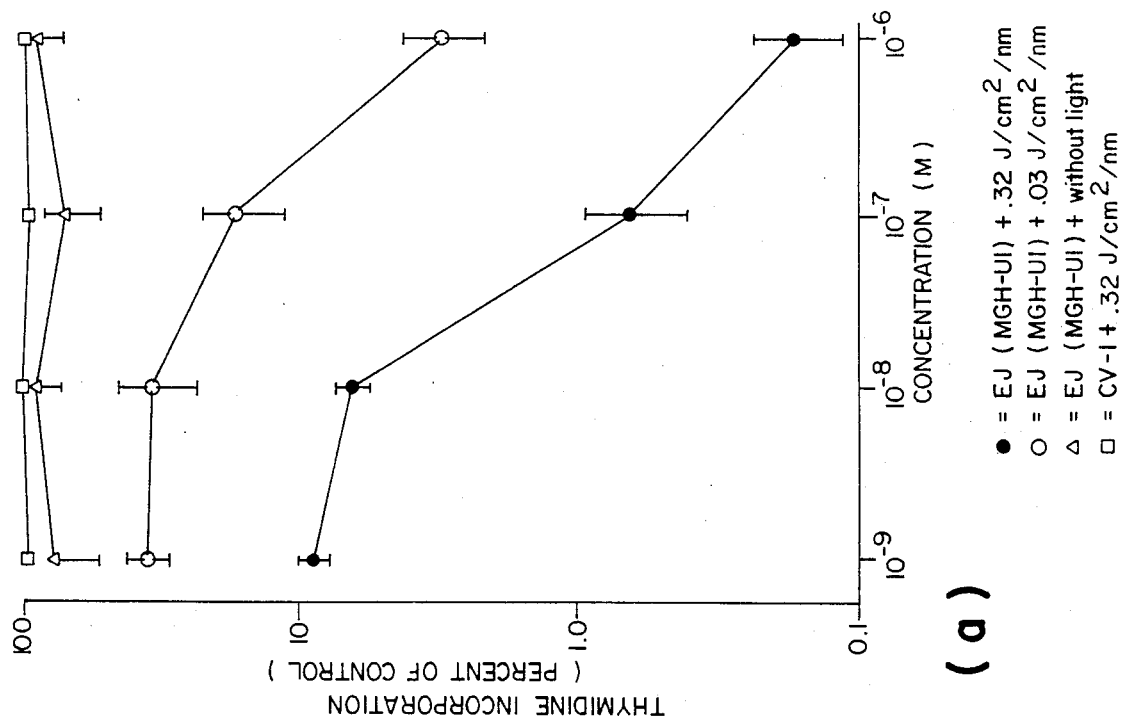

EDKC was subjected to further testing, the results of which are shown in FIG. 2. Subconfluent monolayers of EJ (MGH-U1) cells and control CV-1 monkey kidney cells were incubated with EDKC ($10^{-6}$-$10^{-9}$M) for 20 minutes and washed three times. After 4 hours they were irradiated with 0–640 mJ/cm$^2$/nm laser light. Replicate cultures were pulsed with tritiated thymidine after 12-24 hours, harvested and counted.

FIG. 2a shows the effect of EDKC dose in the dark, and of two different doses of light. There is no significant EJ (MGH-U1) dark toxicity at less than $10^{-6}$M dye, and no CV-1 toxicity with or without light at any of the dye concentrations studied. FIG. 2b shows the effect of different light doses, using $10^{-6}$M and $10^{31\ 7}$M EDKC. Again, the toxicity was selective for carcinoma cells. There is a typical phototoxic killing curve for the EJ (MGH-U1) cells, and an almost 1000-fold enhancement of the low (<20%) dark toxicity was achieved. Trypan blue exclusion and Rh 123 uptake studies showed that the low thymidine incorporation was due to mitochondrial damage and cell death. Using a dye laser rather than the xenon arc source will readily allow at least a 100-fold increase in light dose, which may permit the use of even lower dye concentration with short irradiation times.

Killing Mechanism

The selective retention feature of the invention permits the use of chromophores which kill carcinoma cells by either of the two known photolytic mechanism; i.e., photochemical and thermal killing.

Thermal killing is best achieved using chromophores which have high laser light absorption and rapid internal conversion of electronic excited state energy into heat (preferably faster than $10^{-11}$ sec.). Some cyanine dyes possess these properties, as do some rhodamine derivatives.

Thermal killing also requires good photostability. As shown in Table I, the quantum yield of some of the listed chromophores is less than 0.001 in a non-polar environment, meaning they can absorb more than 1,000 photons before they are destroyed; this is an acceptable level of photostability, although even higher stability would be desirable, as that would permit the use of lower dosgaes of chromophore and higher fluences of light.

Thermal killing was demonostrated for one of the chromophores of Table I, Rhodamine 6G, as follows. Using 20 nsec pulses from a doubled neodinium: YAG laser (530 nm) and $10^{-6}$M rhodamine 6G, mitochondrial-selective thermal damage was achieved in MCF-7 carcinoma cells. (As is desirable in photochemical and thermal killing, the peak absorption band of rhodamine 6G matches the wavelength of the laser.) Mitochondrial damage was assessed by loss of fluorescence of rhodamine 6G and the lack of uptake of Rh 123 applied after irradiation.

Similarly, 50 nsec pulses from a Q-switched ruby laser (694 nm) were used to thermally damage mitochondria in NIH:OVCAR-3 ovarian carcinoma cells stained with Janus green B. For both Janus green and for Rh 6G, it was undesirably necessary to use concentrations that were close to the toxic level without light, and laser powers which were close to the threshold for non-linear, non-specific absorption. The limiting factor for both dyes appears to be the relatively long internal conversion time for the electronic energy to be converted into heat. Inadequate photostability of the dyes may also have been a factor. By using more appropriate dyes with short internal conversion times, or longer pulses, the efficiency of thermal damage processes could be increased.

One such rhodamine derivate which will be expected to perform more efficiently in thermal cell killing is 3,6 bis-indoline-fluoran, which can be synthesized according to the method of Cournoyer et al. U.S. Pat. No. 4,290,950, hereby incorporated by reference. 3,6 dichlorofluoran will be reacted with indoline in dimethylsulfoxide with paratoluene sulfonic acid as a catalyst. The resultant dye will be esterified with acidic ethanol to give the 3,6 bis indoline rhodamine. If necessary, it will be derivatized to maximize mitochondrial uptake and minimize toxicity.

Another desirable property of thermal chromophores is an absorption spectrum in the range of 600–1300 nm; this prevents surrounding blood from absorbing light intended for the chromophore (hemoglobin absorbs primarily at the violet end of the spectrum). The chromophores also preferably have short singlet excited state lifetimes, so they can absorb multiple photons during the laser pulse.

Photochemical cell killing also preferably uses chromophores with peak absorbance in the 600–1300 nm range. Whether photostability is important depends on the mechanism of photochemical cell killing. For chromophores which kill by the interaction with oxygen to produce singlet state oxygen, high photostability is desirable, so that such production continues for as long as possible before the dye breaks down. These chromophores preferably have high intersystem crossing rates to the triplet state, and long triplet lifetimes.

For chromophores which kill by virtue of the degradation of the chromophore to a toxic reaction produce, photostability is generally not desired, since the breakdown of the dye is the process which achieves the desired effect.

Chromophore Synthesis

Some of the chromophores of Table I were synthesized as follows; others can be made by making appropriate modifications in these methods.

1,1'-(3-propylamine hydrobromide)-3,3,3',3'-tetramethylindo-tricarbocyanine bromide (compound 5) was prepared by the following method. Two equivalents of the reactive quaternary salt 1-(3-propylamine hydrobromide)-2,3,3-trimethylindoline bromide and one equivalent of 1-(4-pyridyl)pyridinium chloride hydrochloride were added to pyridine and heated to 110° C. for three hours. The cyan-colored mixture was cooled to room temperature, filtered, washed with acetone, and recrystallized from ethanol to yield metallic green crystals. The dye was further purified by chromatographic separation on a reverse phase $C_{18}$ column using a medium pressure pump and elution with water and water-methanol mixtures.

EDKC (compound 8) was prepared by the method of Hamer in *The Cyanine Dyes and Related Compound* (John Wiley & Sons, N.Y., 1964), as follows. Two equivalents of the active quaternary salt 1-ethyl-1,3-dioxolane lepidinium bromide were pre-dissolved in pyridine at 110° C. One equivalent of ethyl orthoformate was added to this solution and stirred for two hours. The resulting cyan solution was poured into ethyl ether and the precipitate isolated by filtration. The crude dye was dissolved in methylene chloride and placed on a chromatography column packed with silica (Woelm 32-63). The product was eluted with a methanol-methylene chloride mixture under medium pressure and the appropriate fractions collected. Solid dye was obtained by evaporation of the solvent.

Compound 6, an asymmetrical 4,4'-carbocyanine, was prepared using modified methods of Hamer, id, and Ogata (in the same volume). One equivalent of 1-(3-propylphthalimide)-4-(β-acetanilidovinyl)quinolinium bromide was reacted with one equivalent of the betaine 1-(3-sulfopropyl)lepidine in DMSO at 115° C. with one equivalent of triethylamine. The solution was heated for ten minutes, cooled, and the DMSO extracted with ethyl ether to leave a blue residue. This residue was washed with acetone and then crystallized from methanol to give green crystals, which were placed in anhydrous ethanol with two equivalents of hydrazine hydrate and refluxed for four hours. The ethanol was removed under reduced pressure and acetone added to the residues and refluxed for four hours. The mixture was filtered and vacuum-dried to give the 4,4'-carbocyanine.

The 1,1'-diethylvalerate thiacarbocyanine bromide (compound 7) was prepared according to the method of van Dormael (1949) Sci. Ind. Phot. 20, 451. Two equivalents of the active quaternary 1-ethyl valerate-2-methylbenzothiazolium bromide and one equivalent of ethyl orthoformate were heated to 110° C. in pyridine for one hour. The magenta solution was cooled to room temperate and extracted with ethyl ether to leave a solid residue. This crude dye was dissolved in methylene chloride and placed on a chromatography column packed with silica (Woelm 32-36) and eluted with methanol-methylene chloride mixtures under medium pressure.

Therapeutic Applications

Administration of the chromophore is carried out according to methods now used for HPD. Generally, the chromophore is dissolved in physiological saline and injected intravenously or intraperitoneally. The chromophore in solution can also in some instances be administered subcutaneously, intralesionally, or topically, in a suitable carrier vehicle which facilitates tissue uptake. Chromophore concentration is generally such that between 0.1 and 100 mg/kg body weight of chromophore is delivered to the patient, to yield a concentration in carcinoma cells sufficient for light-induced killing (generally $10^{-7}$–$10^{-5}$M). Preferably a time interval passes before laser light is used, to give the chromophore time to reach the target tissues and to preferentially dissipate from normal cells, enhancing the differential chromophore concentration in carcinoma cell mitochondria compared to normal cells. This time interval is generally two to twenty-four hours, most preferably about four to eight hours.

Light-induced killing of carcinoma cells according to the invention can be carried out on any carcinoma cells which are accessible to light from conventional sources (e.g., a xenon arc lamp) or from a laser, via the body surface or via optical fibers; delivery of laser light is carried out according to the well-known methods currently used for HPD-mediated laser therapy.

The treatment will be most effective for carcinomas concentrated on organ or skin surfaces, e.g. transitional cell carcinoma of the bladder, cutaneous T cell lymphoma, squamous cell carcinoma and adenocarcinoma of the skin, respiratory and gastrointestinal carcinomas, and ovarian carcinoma. In the latter disease, the peritoneal surfaces can be readily exposed to laser radiation, intra-operatively and for long periods of time, using a laproscopically-directed optical fiber.

OTHER EMBODIMENTS

Other embodiments are within the following claims. For example, classes of chromophores other than cyanines and rhodamines can be used, synthetically modified to give desired properties. For example, rose bengal can be made to absorb above 600 nm by changing it to a fluorene structure.

We claim:
1. A method of killing carcinoma cells associated with normal cells using light of predetermined wavelength, said method comprising
   (a) contacting said cells with a chromophore at a predetermined concentration, said chromophore being characterized in that
      it is positively charged and sufficiently lipophilic to be taken up by said carcinoma cells and their mitochondria,
      it is retained substantially longer in the mitochondria of said carcinoma cells than in the mitochondria of said normal cells, or more of said chromophore is taken up by said carcinoma cells than by said normal cells contacted with said chromophore,
      it has a therapeutic index for light-induced cell killing of at least 500 for light of said predetermined wavelength; and
      it has a therapeutic ratio for light-induced killing of at least 50 for light of said pre-determined wavelength; and
   (b) exposing said contacted carcinoma cells to said light.
2. The method of claim 1 wherein said chromophore is taken up by said normal cells and said carcinoma cells, and there is a time interval between steps (a) and (b) which is sufficiently long to permit dissipation from said normal cells of a sufficient amount of said chromophore to prevent killing of at least 80% of said normal cells when said cells are exposed to said light, and sufficiently short to ensure that enough of said chromophore is retained by said mitochondria of said carcinoma cells to cause at least 80% of said carcinoma cells contacted with said chromophore to be killed when exposed to said light.
3. The method of claim 1 wherein exposure of said chromophore to said light causes said chromophore in said carcinoma cell mitochondria to participate in a chemical reaction yielding a reaction product more cytotoxic than said chromophore.
4. The method of claim 1 wherein exposure of said chromophore to said light causes thermal destruction of said carcinoma cells.
5. The method of claim 1 wherein said chromophore strongly absorbs said light at said predetermined wavelength, said wavelength being above 600 nm.

* * * * *

UNITED STATES PATENT AND TRADEMARK OFFICE
CERTIFICATE OF CORRECTION

PATENT NO. : 4,651,739
DATED : March 24, 1987
INVENTOR(S) : Oseroff et al.

It is certified that error appears in the above-identified patent and that said Letters Patent are hereby corrected as shown below:

Column 6, line 49, "$10^{31}$ 7M" should be --$10^{-7}$ M--.

Column 6, line 65, "mechanism" should be --mechanisms--.

Column 7, line 12, "dosgaes" should be --dosages--.

Column 7, line 14, "demonostrated" should be --demonstrated--.

Column 8, line 65, "room temperate" should be --room temperature--.

Signed and Sealed this

Eighteenth Day of August, 1987

Attest:

DONALD J. QUIGG

Attesting Officer     Commissioner of Patents and Trademarks